(12) United States Patent
Tsuchiya et al.

(10) Patent No.: US 7,887,868 B2
(45) Date of Patent: *Feb. 15, 2011

(54) LIQUID SEASONING

(75) Inventors: Shigemi Tsuchiya, Tokyo (JP); Yoko Seo, Tokyo (JP); Jun Kohori, Tokyo (JP); Ryuji Ochiai, Haga-gun (JP); Atsushi Suzuki, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/436,517

(22) Filed: May 19, 2006

(65) Prior Publication Data

US 2006/0275346 A1 Dec. 7, 2006

Related U.S. Application Data

(63) Continuation-in-part of application No. 11/180,734, filed on Jul. 14, 2005.

(30) Foreign Application Priority Data

Nov. 12, 2004 (JP) ............................. 2004-329850

(51) Int. Cl.
*A23L 1/40* (2006.01)
*A23L 1/237* (2006.01)
*A61K 31/05* (2006.01)

(52) U.S. Cl. .................. 426/589; 426/649; 514/732

(58) Field of Classification Search ................ 426/589, 426/7, 18, 648, 649, 60; 514/732; 424/115
See application file for complete search history.

(56) References Cited

U.S. PATENT DOCUMENTS

| 4,382,964 | A | 5/1983 | Noda et al. |
| 4,795,595 | A | 1/1989 | Agnes et al. |
| 5,562,942 | A | 10/1996 | Koh et al. |
| 6,159,529 | A | 12/2000 | Uchida et al. |
| 7,666,409 | B2 * | 2/2010 | Tsuchiya et al. ............ 424/115 |
| 2002/0106424 | A1 | 8/2002 | Ogawa et al. |
| 2003/0203096 | A1 * | 10/2003 | Hamm et al. ............... 426/589 |
| 2005/0123670 | A1 | 6/2005 | Vasquez |
| 2005/0181069 | A1 * | 8/2005 | McCleary ................... 424/686 |
| 2005/0181083 | A1 | 8/2005 | Takagaki et al. |
| 2006/0115517 | A1 | 6/2006 | Tsuchiya et al. |
| 2006/0115518 | A1 | 6/2006 | Tsuchiya et al. |
| 2008/0057174 | A1 | 3/2008 | Yamakoshi et al. |

FOREIGN PATENT DOCUMENTS

| JP | 58-209957 | 12/1983 |
| JP | 59-55165 | 3/1984 |
| JP | 2-167052 | 6/1990 |
| JP | 04-279597 | 10/1992 |
| JP | 5-7987 | 1/1993 |
| JP | 6-97972 | 12/1994 |
| JP | 7-227245 | 8/1995 |
| JP | 2675254 | 7/1997 |
| JP | 10-66540 | 3/1998 |
| JP | A 11-000127 | 1/1999 |
| JP | 11-032693 | 2/1999 |
| JP | 11-187841 | 7/1999 |
| JP | 3117779 | 12/2000 |
| JP | 3166077 | 3/2001 |
| JP | 2001-240600 | 9/2001 |
| JP | 2001-245627 | 9/2001 |
| JP | 2001-352940 | 12/2001 |
| JP | 2002-53595 | 2/2002 |
| JP | 2002-165577 | 6/2002 |
| JP | 2002-233333 | 8/2002 |
| JP | 2002-300862 | 10/2002 |
| JP | 2002-360289 | 12/2002 |
| JP | 2003-169659 | 6/2003 |
| JP | 2004-147560 | 5/2004 |
| JP | 2004-187501 | 7/2004 |
| JP | 2004194515 A * | 7/2004 |
| JP | A 2004-194515 | 7/2004 |
| JP | 2004-290129 | 10/2004 |
| JP | A 290088 | 10/2004 |
| JP | A 2006-87328 | 4/2006 |
| JP | 2006-166906 | 6/2006 |

OTHER PUBLICATIONS

Hubert C. Stanton, Mode of Action of Gamma Amino Butyric Acid on the Cardiovascular System $(_1)$, $(_2)$, Arch. Int. Pharmacodyn., vol. 143, No. 1-2, 1963, pp. 195-204.

"Components of Brewed Substances", Brewing Society of Japan, Dec. 10, 1999, p. 449 (with English translation).

* cited by examiner

*Primary Examiner*—Kevin Weddington
(74) *Attorney, Agent, or Firm*—Oblon, Spivak, McClelland, Maier & Neustadt, L.L.P.

(57) ABSTRACT

A liquid seasoning, comprising:
(A) 3.55% by weight or less of sodium;
(B) 0.5 to 4.2% by weight of potassium; and
(C) 0.05 to 20% by weight of a substance having an antihypertensive effect. Salty taste is sufficiently provided despite its low sodium concentration, and pharmacological functions such as an antihypertensive effect are also provided at a high level.

26 Claims, 1 Drawing Sheet

SBP rate-of-change after 6 hours of administration

LIQUID SEASONING

REFERENCE TO RELATED APPLICATIONS

This application is a continuation-in-part of a copending U.S. patent application Ser. No. 11/180,734 filed Jul. 14, 2005, which is incorporated herein by reference and which claims priority under 35 USC 119(a) to Japanese patent application No. 2004-329850 filed Nov. 12, 2004, the teachings of which are incorporated herein by reference and priority to which is claimed herein.

FIELD OF THE INVENTION

The present invention relates to a liquid seasoning.

BACKGROUND OF THE INVENTION

With an increase in interest in physiological functions of various ingredients contained in food products in recent years, the number of cases in which the Ministry of Health, Labour and welfare of JAPAN authorizes food products containing ingredients contributing to such physiological functions and biological actions as Food for Specified Health Use (FOSHU) is increasing. These food products have been commercialized in the form of daily dishes such as beverages, yogurt, soup, miso soup, and hamburgers as well as tablet candies and tablets, and it has been recommended to take these food products once or twice a day.

Examples of physiological functions include sympathetic nerve inhibiting effect, antioxidant effect, antihypertensive effect, liver function-improving effect and the like, and materials having these functions are sympathetic nerve inhibiting substances, polyphenols, peptides and the like. Humans are subject to stresses from daily lives and their sympathetic nerves are excited as a result, leading to lifestyle-related diseases. Thus, continuous intake of the substances which suppress the excitation of sympathetic nerves has become one of the preventing means for such diseases. Among them, γ-aminobutyric acid is a substance contained in food products and having a high level of safety, and it has been proposed a technique for increasing the content thereof in food products and for adding it to food products (JP-A-2004-147560, JP-A-2003-169659, JP-A-2001-352940, and JP-A-1995-227245).

γ-aminobutyric acid is known to have an antihypertensive effect by which excretion of sodium ions into urine is facilitated in response to excessive ingestion of sodium chloride other than a sympathetic nerve inhibiting effect (Hubert C. Stanton, Archint. Pharmacodyn., 143, p195-204, 1963). Thus, there has been numerous techniques in which γ-aminobutyric acid is used in combination with soy sauce which is a typical food product containing a large amount of sodium chloride (JP-A-2004-187501, JP-A-2002-360289, JP-A-2002-300862, and Japanese Patent No. 3166077). However, since the content of γ-aminobutyric acid within the food product is low, it is necessary to eat a large amount of foods in order to take an effective amount of γ-aminobutyric acid. This leads to the excessive ingestion of sodium chloride, which may result in unfavorable outcomes, meaning the effect of ingesting γ-aminobutyric acid is lessened. In addition, since the production of γ-aminobutyric acid involves the use of a large amount of glutamic acid as a basic ingredient, flavors may be adversely affected by mixing a large amount of γ-aminobutyric acid with a food product depending on a degree of purification.

Examples of substances which have physiological functions include polyphenols. Polyphenols are known to have physiological functions such as an antioxidant effect, an antihypertensive effect, and a liver-function improving effect. In particular, the antihypertensive effect has come to attract attention, and a food product into which polyphenols having such effects are blended was qualified as a Food for Specified Health Use.

In addition, a substance which has physiological functions is peptide. Peptide is known to have physiological functions such as an antihypertensive effect and a liver-function improving effect. In particular, the antihypertensive effect provided by an angiotensin converting enzyme inhibitory effect has come to attract attention, and a food product into which peptide having such effects is blended has been authorized as a Food for Specified Health Use. Lactic acid bacteria beverages containing lactotripeptide, soft drinks containing caseindodecapeptide, powdered soup and processed food (granulated type) containing dried bonito peptide and the like are commercially available.

SUMMARY OF THE INVENTION

The present invention relates to a liquid seasoning, comprising:
(A) 3.55% by weight or less of sodium;
(B) 0.5 to 4.2% by weight of potassium; and
(C) 0.05 to 20% by weight of a substance having an antihypertensive effect.

DETAILED DESCRIPTION OF THE INVENTION

Figure 1:
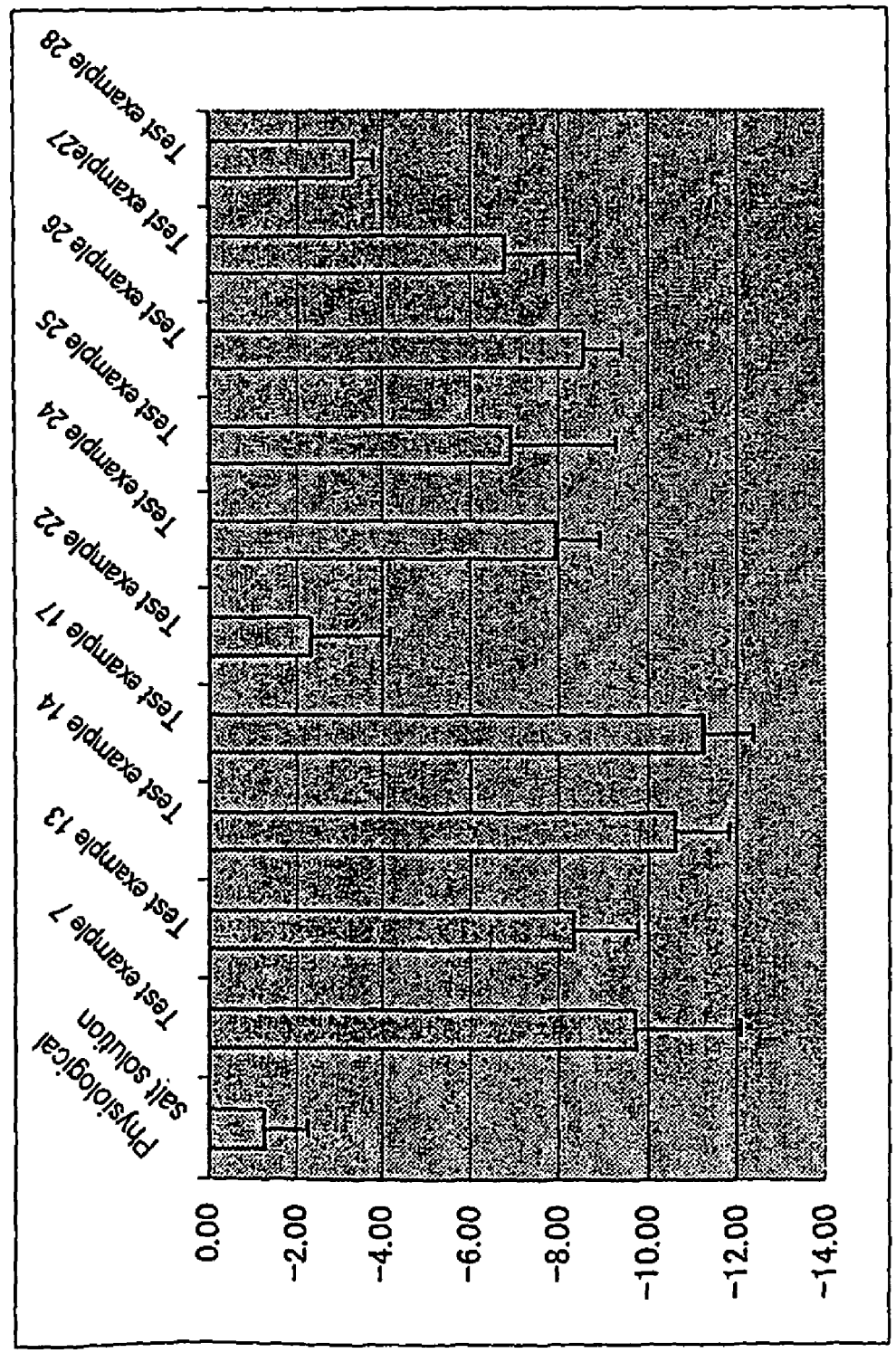
FIG. 1 illustrates the effect of lowering blood pressure in the contraction stage six hours after administration of the liquid seasoning.

It is believed that, if a substance having an antihypertensive effect is blended into a seasoning, especially a liquid seasoning, which is widely used for seasoning in cooking, the antihypertensive effect is provided in an usual dietary life without a particular consciousness of lowering a blood pressure. In addition, it is expected that blending such substances into soy sauce, among other liquid seasonings, produces the above described effect considering ingestion frequencies and intake amounts of soy sauce. Although there are various kinds of soy sauce, it is favorable to use a soy sauce containing a decreased amount of sodium chloride compared with regular soy sauce considering objective is to bring about an antihypertensive effect. However, the prior art has not yet solved some problems such as inferior seasoning caused by using the soy sauce in combination with the substance having an antihypertensive effect, and sodium chloride ingestion by consumption of large amount of food products. For these reasons it is still not desirable to intake such food products continuously. In particular, if the above described substance is used in combination with a reduced-salt food typified by low-salt soy sauce, there is another problem such as the necessity of strengthening a salty taste because the reduced-salt food is insufficient in its salty taste. There have been various techniques for improving the flavor of reduced-salt foods (Japanese Patent No. 2675254, JP-A-1994-97972, JP-A-1998-66540, JP-A-2001-245627, JP-A-2002-165577, JP-A-1993-007987, and JP-A-1999-187841) each of which has achieved a certain effect, but it can not be said that these techniques are sufficient. In particular, these techniques are insufficient in terms of compatibility between the reduction of sodium chloride concentration and impartment of the salty taste.

The inventors of the present invention have searched for measures for improving the flavor of a liquid seasoning which contains a substance having an antihypertensive effect and for providing a salty taste even when the sodium concentration is 3.55% by weight or less (the sodium chloride concentration is 9% by weight or less), and consequently, have found that it becomes possible to obtain a flavorful liquid seasoning having a strengthened salty taste, whose flavor does not deteriorate even when the substance having an antihypertensive effect is blended therein by lowering the sodium concentration to 3.55% by weight or less (the sodium chloride concentration to 9% by weight or less) and setting the potassium concentration at 0.5 to 4.2% by weight. In addition, the inventors have found that continuous ingestion becomes possible and the antihypertensive effect is kept at a higher level.

The term "low-salt soy sauce" used herein means "soy sauce" and "a soy sauce processed product" whose sodium content in 100 g of a product is 3550 mg (9 g, calculated in terms of sodium chloride) or less, and is not limited to special use food products for patients who receive medical treatments in accordance with the nutrition improvement law of JAPAN. The term "soy sauce" means a liquid seasoning defined by Japanese Agricultural Standards, and the term "soy sauce processed product" means a liquid seasoning which is used for the same purpose as "soy sauce" and which is obtained by adding seasonings, acidulants, flavor, soup stocks, extracts and the like to the "soy sauce" as defined by Japanese Agricultural Standards. The term "soy sauce" described herein forms an identical concept to the term "soy sauce" defined by Japanese Agricultural Standards. In addition, "a liquid seasoning" described herein is intended to include the seasoning complying with the requirements of the present application although being out of the standards of the above-described low-salt soy sauce or the standard for a low-salt soy sauce. Contents of blending materials are usually expressed in w/v % in the art of liquid seasoning, but in the present application, a blending amount of each ingredient is expressed in % by weight of a total amount of the liquid seasoning (w/w %). Therefore, in the case of a nitrogen content in soy sauce for example, "1.6% by weight" corresponds to "1.9 w/v %."

Preferably, the content of (A) sodium in a liquid seasoning of the present invention is 3.55% by weight or less, preferably 1.18 to 3.55% by weight, more preferably 2.75 to 3.5% by weight, even more preferably 3.1 to 3.4% by weight, and even more preferably 3.2 to 3.4% by weight in view of the antihypertensive effect and flavor (a salty taste is sufficiently recognized). The term "content" herein means a proportion to the total amount of the liquid seasoning unless otherwise specified below. Sodium chloride may be used as (A) sodium in the liquid seasoning of the present invention. The content of sodium chloride in the liquid seasoning of the present invention is 9% by weight or less, preferably 3 to 9% by weight, more preferably 7 to 9% by weight, even more preferably 8 to 9% by weight, and even more preferably 8.2 to 8.8% by weight in view of the antihypertensive effect and flavor (a salty taste is sufficiently recognized).

Preferably, the content of (B) potassium in the liquid seasoning of the present invention is 0.5 to 4.2% by weight, more preferably 1 to 3.6% by weight, even more preferably 1.5 to 3.1% by weight, and even more preferably 1.7 to 2.7% by weight, from the view point of reducing the bitter taste and strengthening the salty taste in spite of having a low sodium content. A preferable potassium-containing compound is potassium chloride because it has a salty taste but a reduced foreign taste. When potassium chloride is used, the content thereof is preferably 1 to 8% by weight, more preferably 1 to 7% by weight, even more preferably 2 to 6% by weight, and even more preferably 3 to 5% by weight.

Examples of methods for adjusting the sodium chloride content and the potassium content within the above described ranges include: a method of producing soy sauce by the use of a mixed solution of sodium chloride and potassium chloride for example as a mother water for example; a method of mixing soy sauce obtained by using a solution of potassium chloride alone as a mother water with soy sauce obtained by using a salt solution as a mother water; a method of adding potassium chloride to a desalted soy sauce from which sodium chloride is eliminated by electrodialysis, a membrane treatment or the like, the soy sauce being originally a regular soy sauce made by using a sodium chloride solution as a mother water.

The liquid seasoning of the present invention contains preferably 0.05 to 20% by weight of (C) a substance having an antihypertensive effect, and more preferably 0.1 to 10% by weight, and even more preferably 0.2 to 5% by weight in view of the antihypertensive effect and the flavor. In the aspects of the present invention, examples of (C) the substance having an antihypertensive effect include sympathetic nerve inhibiting substances, polyphenols, and peptides having an angiotensin conversion inhibitory effect. Examples of the sympathetic nerve inhibiting substances are γ-aminobutyric acid and taurine as well as salts thereof, and one or more substances selected from these substances may be used. Among others, γ-aminobutyric acid is preferable in terms of the antihypertensive effect, safety, flavor and the like. It is possible to preferably use γ-aminobutyric acid which has been extracted from food products and which has been produced by subjecting L-glutamic acid-containing food products to the decarboxylase. Examples of such substances which are optimally used as the liquid seasonings include fish sauce mash, and a compressed solution thereof, and fermented fish sauce. In addition, examples of optimum substances used for the liquid seasoning of the present invention include substances made from fermented soybeans, rice germ, or rice bran, and these may be preferably used because of their impaired flavors. Further, γ-aminobutyric acid at a purity of 100% has recently been obtained by extracting and purifying the crude products obtained by fermentation, and this may be more preferably used because flavor is not impaired.

In an aspect of the present invention, taurine extracted from food products (fish and shells) may be preferably used. A blending amount of taurine into the liquid seasoning of the present invention is preferably 0.05 to 5% by weight, more preferably 0.2 to 3% by weight, and even more preferably 0.5 to 2% by weight from the viewpoint of the antihypertensive effect and the flavor.

In an aspect of the present invention, one type of polyphenol is preferably a phenolic compound in which one or more, and preferably two or more hydroxyl groups are attached to a benzene ring. Examples of such compounds include flavonoid, tannin, phenolic acid and the like derived from plants. Glycosides thereof may also be used. Examples of more preferable polyphenols are caffeoylquinic acids, feruloylquinic acids, flavonols, flavanols, flavanones, flavones, isoflavones, and anthocyanidins. Specific examples include catechin, epicatechin, gallocatechin, epigallocatechin, rutin, quercitrin, isoquercitrin, quercetin, myricitrin, myricetin, daizein, daizin, glycitein, glycitin, genistein, genistin, myricitrin, hesperidin, methylhesperidin, neohesperidin, hesperetin, naringin, naringenin, prunin, astragalin, kaempferol, apiin, apigenin, delphinidin, delphin, nasunin, peonidin, peonin, petunin, peonidin, malvidin, malvin, enin, cyanidin, leucocyanidin, cyanin, chrysanthemin, keracyanin, idein, mecocyanin, pelargonidin, callistephin, a derivative thereof, and a mixture consisting of two or more selected from among the aforementioned substances. Examples of such a derivative include an acetylated product, a malonylated product, a methylated product, and a sugar-binding product. A sugar-binding product, in which one or more molecules of sugars, such as glucose, rhamnose, galactose, rutinose, neohesperidose, or apiosyl glucose, are bound to one molecule of polyphenol via a covalent bond is preferred. Preferably 1 to 20, more preferably 2 to 10 molecules of such sugars bind to the above polyphenol. Of these, caffeoylquinic acids are preferable because they have a stable and permanent antihypertensive effect. In addition, the polyphenols in the present invention include the compounds which substituted a part or all of the methoxyl groups for hydroxy groups in the polyphenol molecules.

Caffeoylquinic acids include isomers and analogues thereof, and the present invention may use pure isomers, analogues, or a mixture thereof. Specifically, caffeoylqunic acids in the present invention include 3-caffeoylquinic acid, 4-caffeoylquinic acid, 5-caffeoylquinic acid (chlorogenic acid), 3,4-dicaffeoylquinic acid, 3,5-dicaffeoylquinic acid, 4,5-dicaffeoylquinic acid, 3-feruloylquinic acid, 4-feruloylquinic acid, 5-feruloylquinic acid, 3-feruloyl-4-caffeoylquinic acid and the like.

Caffeoylquinic acids in the form of a salt may improve its water solubility and increase its physiological function. Pharmacologically accepted salt is preferably used as the above described salt. As basic substances used for producing the above described salt, it is possible to use hydroxides of alkali metals such as lithium hydroxide, sodium hydroxide, and potassium hydroxide; hydroxides of alkaline earth metals such as magnesium hydroxide and calcium hydroxide; inorganic bases such as ammonium hydroxide; basic amino acids such as arginine, lysine, histidine, and ornithine; organic bases such as monoethanolamine, diethanolamine, and triethanolamine for example, and among these, hydroxides of alkali metals or alkaline earth metals are preferable. In the present invention, the above described salt may be prepared and then added to a composition comprising other components, or alternatively, caffeoylquinic acid and the salt-forming component may be separately added to the above described composition to form therein the above described salt.

As the natural extracts containing caffeoylquinic acids, it is possible to use an extract which has been extracted from a plant containing a large amount of caffeoylquinic acids such as coffees, cabbages, lettuces, artichokes, tomatoes, eggplants, potatoes, carrots, apples, pears, plums, peaches, apricots, cherries, sunflowers, jew's-marrows (mulukhiya), and sugarcanes for example.

An example of raw coffee bean extracts is "Flavor Holder" produced by T. Hasegawa Co., Ltd., an example of apple extracts is "Apple Phenon" produced by Nikka Whisky Distilling Co., Ltd., and an example of sunflower seed extracts is "Heliant S-100" produced by Dainippon Ink & Chemicals. Inc. The content of caffeoylquinic acids in the plant extract to be used is preferably 1 to 80% by weight, more preferably 1 to 50% by weight, and even more preferably 1 to 40% by weight from the viewpoint of the antihypertensive effect.

In an aspect of the present invention, isoflavone extracted from soybeans may be preferably used. In particular, glycosides such as prunetin (5,4'-dihydroxy-7-methoxy compound) and irigenin (5,7,3'-trihydroxy-6,4',5'-trimethoxy compound) may be preferably used as substances which are soluble in the liquid seasoning.

A blending amount of polyphenols into the liquid seasoning of the present invention is preferably 0.1 to 5% by weight, more preferably 0.2 to 3% by weight, even more preferably 0.25 to 2% by weight, and even more preferably 0.5 to 2% by weight from the view point of the antihypertensive effect and the flavor. The blending amount of polyphenols herein means an amount of polyphenols added to the liquid seasoning. An amount of polyphenols equal to or less than 0.1% by weight does not provide a sufficient antihypertensive effect. In addition, the blending of 5% by weight or more of polyphenols is not preferable because of an overemphasized foreign taste.

In an aspect of the present invention, a peptide having an angiotensin conversion inhibitory activity may be one derived from a raw material of a food product. In particular, it is preferable to use peptide derived from milk, peptide derived from grain, and peptide derived from fish meat. Preferable peptides derived from grain herein are peptides whose molecular weight is 200 to 4000, and peptide derived from corn whose molecular weight is 200 to 4000 is preferred. In addition, a peptide having a molecular weight of 200 to 4000 obtained by treating corn protein, soy protein, wheat protein or the like with a protease, a peptide having a molecular weight of 200 to 4000 obtained by treating corn protein with an alkaline protease (JP-A-1995-284369) is preferable. As peptide derived from fish meat, it is preferable to use peptide derived from fish meat having a molecular weight of 200 to 10000, and more preferably a peptide having a molecular weight of 200 to 10000 obtained by treating fish meat of mackerel, bonito, tuna, saury or the like with a protease, and even more preferably a peptide having a molecular weight of 200 to 10000 obtained by treating bonito protein with a protease.

The intensity of an angiotensin converting enzyme inhibitory activity is expressed as a concentration at which the activity of the angiotensin converting enzyme is suppressed by 50% (IC50). When the IC50 of a peptide which has the angiotensin converting enzyme inhibitory activity used for the present invention is about 50 to 1000 μg/mL, an antihypertensive effect may be expected in the low-salt soy sauce system.

Examples of commercial products of peptide which may be blended in the present invention include Peptino (Nihon Shokuhin Kako Co., Ltd., IC50: 130 μg/mL) as peptide derived from corn, Glutamine Peptide GP-1 (Nisshin Pharma Inc., IC50: 508 μg/mL) as peptide derived from wheat, HiNeute (Fuji Oil Co., Ltd., IC50: 455 μg/mL) as peptide derived from soybeans, and PeptideStraight (Nippon Supplement Inc., IC50: 215 μg/mL) as peptide derived from bonito.

The angiotensin converting enzyme inhibitory activity of the above described peptide may be measured by employing ACE color (Fujirebio Inc.) which is a simple and more reproducible measurement kit using a synthetic substrate, p-hydroxybenzoyl-glycyl-L-histidyl-L-leucine, for example. A blending amount of this peptide into the liquid seasoning is preferably 0.5 to 20% by weight, and more preferably 1 to 10% by weight, and even more preferably 2 to 5% by weight from the viewpoint of the antihypertensive effect and the flavor.

In the present invention, it is possible to blend vinegar, nicotianamine, nucleic acid derivatives, soy sauce cake, sphingolipid or the like as a substance having an antihypertensive effect, in addition to the above described substances, preferably by the amount of 0.05 to 5% by weight, and more preferably 0.2 to 3% by weight, and even more preferably 0.5 to 2% by weight.

In an aspect of the present invention, a nitrogen content is preferably 1.6% by weight or more in the liquid seasoning excluding the component (C) content therefrom, because the flavor is not spoiled despite the inclusion of substances having an antihypertension effect, and the salty taste is strengthened despite the low sodium or sodium chloride content, and further, a bitter taste is not provided. In addition, the nitrogen content is more preferably 1.6 to 2% by weight. Although it has been said that the taste of soy sauce usually becomes mild and the salty taste becomes subtle when the nitrogen content is increased, it was completely unexpected that the salty taste was improved by adjusting the nitrogen content within the above described range in the case of soy sauce in which the sodium or sodium chloride content was low and potassium was included.

Although the nitrogen content in regular soy sauce is 1.2 to 1.6% by weight, the nitrogen content equal to or more than 1.6% by weight may be achieved by subjecting soy sauce after being brewed in an usual manner to a concentration step and a desalting step. For example, there exists a method of adjusting the ratio of dilution with a water based volatile component while removing sodium or sodium chloride by a salt restriction and concentration method, and a method of concentrating the nitrogen content simultaneously by utilizing the transfer of hydrated water of ions caused when removing sodium or sodium chloride, by an electrodialyzer, for example. In addition, there also exists a method of increasing the nitrogen content in low-salt soy sauce whose sodium or sodium chloride content is lower than regular soy sauce by employing RO membranes or vacuum concentration, or conversely a method of desalting soy sauce whose nitrogen content is high such as tamari soy sauce or refermented soy sauce.

In an aspect of the present invention, the nitrogen content equal to or more than 1.6% by weight may be achieved by adding amino acid seasonings and the like in addition to the above described method. For example, it is possible to blend one or more of glycine, alanine, phenylalanine, cystine, threonine, tyrosine, isoleucine, glutamic acid, aspartic acid, histidine, lysine, arginine, or alternatively sodium salt, potassium salt, or hydrochloride thereof. Among these, glutamic acid and aspartic acid are preferable from the viewpoint of continuous salty taste. The contents of amino acid seasonings, when converted into free amino acid, are preferably as follows: glycine is more than 0.3% by weight, alanine is more than 0.7% by weight, phenyl alanine is more than 0.5% by weight, cystine is more than 0% by weight, threonine is more than 0% by weight, tyrosine is more than 0.2% by weight, isoleucine is more than 0.5% by weight, glutamic acid is more than 1.3% by weight, aspartic acid is more than 0.7% by weight, histidine is more than 0.1% by weight, lysine is more than 0.4% by weight, arginine is more than 0.5% by weight. And respective upper limits thereof are preferably as follows: glutamic acid is 2% by weight or less, aspartic acid is 3% by weight or less, and others are 1.5% by weight or less.

Further, in an aspect of the present invention, the liquid seasoning preferably contains nucleic acid seasonings, organic acid salt seasonings, acidulants and the like, because a salty taste can be strengthened synergistically, and a bitter taste as well as a salty taste can be weakened and the flavor of soy sauce can be strengthened. Examples of the nucleic acid seasonings are sodium salt, potassium salt, or calcium salt of 5'-guanylic acid, 51-inosinic acid or the like. The content of the nucleic acid seasoning is preferably 0 to 0.2% by weight, and more preferably 0.01 to 0.1% by weight.

As the organic acid salt seasoning, it is preferable to use sodium salt, potassium salt and the like of lactic acid, succinic acid, malic acid, citric acid, tartaric acid, gluconic acid and the like. Among these, disodium succinate and sodium gluconate are preferable. The content of the above described substance is preferably 0 to 0.3% by weight, and more preferably 0.05 to 0.2% by weight.

Examples of the acidulants are lactic acid, succinic acid, malic acid, citric acid, tartaric acid and the like. Among these, lactic acid, malic acid, and citric acid are preferable, and lactic acid is more preferable. The content of lactic acid is preferably 0 to 2% by weight, and more preferably 0.3 to 1% by weight. In addition, respective contents of malic acid and citric acid are preferably 0 to 0.2% by weight, and more preferably 0.02 to 0.1% by weight.

In an aspect of the present invention, the pH value of the liquid seasoning is preferably 3 to 6.5, and more preferably 4 to 6, and even more preferably 4.5 to 5.5 from the viewpoint of keeping the flavor from deteriorating. In addition, it is preferable to have some characteristic values such as 4 to 9% by weight of a chlorine content and 20 to 45% by weight of a solids content.

In addition, ammonium chloride and calcium lactate are also effective as additives which strengthen the salty taste of liquid seasonings, however, they are not preferably suitable for soy sauce which also has the function of a general-purpose seasoning because when cooked with the blended soy sauce, the former may present a foreign taste and the latter harden the food product to be cooked. In addition, in an aspect of the present invention, ethanol, mirin, brewed vinegar, sweetener or the like may be added to the liquid seasoning if necessary so as to be applied to various soy sauce-processed products such as a dipping sauce or marinade sauce.

The liquid seasoning of the present invention has an effect of significantly improving hypertension by continuous consumption. Therefore, it is possible to display "suitable for a person concerned with his/her blood pressure", "suitable for a person whose blood pressure is high", "capable of lowering blood pressure", "capable of adjusting the blood pressure" and the like on the surface of a package of the liquid seasoning of the present invention.

EXAMPLE

The following examples further describe and demonstrate embodiments of the present invention. The examples are given solely for the purpose of illustration and are not to be construed as limitations of the present invention.

[Preparation of Base Soy Sauce]

A commercially available low-salt soy sauce D (a nitrogen concentration of 1.5% by weight, a sodium concentration of 3.18% by weight (a sodium chloride concentration: 8.1% by weight), a potassium concentration of 0.38% by weight) was vacuum-concentrated and treated with volatile water and sodium chloride so as to eventually obtain a low-salt soy sauce A in which the nitrogen concentration was 1.8% by weight, the sodium concentration was 3.34% by weight (the sodium chloride concentration of 8.5% by weight), and the potassium concentration was 0.45% by weight. In addition, a commercially available low-salt soy sauce C (a nitrogen concentration of 1.4% by weight, the sodium concentration of 3.18% by weight (the sodium chloride concentration: 8.1% by weight), a potassium concentration of 0.26% by weight) was vacuum-concentrated and treated with volatile water and sodium chloride so as to eventually obtain a low-salt soy sauce B in which the nitrogen concentration was 1.85% by weight, the sodium concentration was 3.30% by weight (the sodium chloride concentration of 8.4% by weight), and the potassium concentration was 0.33% by weight.

(1) Test Examples 1 to 31

The above described low-salt soy sauce A, B, C, and D were used as base soy sauces, to which potassium chloride, acidulant, nucleic acid seasoning, amino acid seasoning, and substances having an antihyperteisive effect are respectively added in order to prepare liquid seasonings having compositions as listed in Table 1. As substances having an antihypertensive effect, a polyphenol preparation A (extracted from Robusta raw coffee beans with hot water for 4 hours, and the extract was treated with an adsorbent (activated carbon, white clay) and concentrated, and then spray-dried. It had about 40% of caffeoylquinic acids), a polyphenol preparation B (spray-dried RC-30 supplied by T. Hasegawa Co., Ltd.; it had about 54% of caffeoylquinic acids), γ-aminobutyric acid, peptide A (Nippon Supplement Inc. PeptideStraight), and peptide B (Nihon Shokuhin Kako Co., Ltd. Peptino) were added to the above described liquid seasonings, so as to prepare the liquid seasonings having compositions as listed in Table 1.

(2) Measurement Method of Sodium Content

The content of sodium was measured by an atomic absorption photometer (Type Z-6100 Hitachi Polarized Zeeman Atomic Absorption Photometer). The content of sodium chloride was obtained by converting the obtained value of the sodium content.

(3) Measurement Method of Potassium

The content of potassium was measured by the same instrument as in the case of the above described sodium concentration measurement.

(4) Measurement Method of Nitrogen Content

The nitrogen concentration was measured by a total nitrogen analyzer (Mitsubishi Kasei Corp. Type TN-05) Table 1 shows a value of nitrogen content in the liquid seasoning excluding therefrom (C) a substance having an antihypertensive effect.

(5) Sensory Evaluation Method

The obtained low-salt soy sauce was subjected to a sensory evaluation in which salty taste and bitter taste of this soy sauce was evaluated by a panel of 10 persons. An overall judgment of this soy sauce was also made. Respective evaluation standards are described below, and the obtained results are shown in Table 1.

(Evaluation Standards of Salty Taste)
1: equivalent to low-salt soy sauce (corresponding to 9% by weight of sodium chloride)
2: about medium between low-salt soy sauce and regular products (ordinary products) (corresponding to 14% by weight of sodium chloride)
3: slightly weaker compared with regular products (ordinary products)
4: equivalent to regular products (ordinary products)
5: stronger than regular products (ordinary products)

(Evaluation Standards of Bitter Taste)
1: none
2: subtly felt
3: slightly felt
4: felt
5: strongly sense (Evaluation Standards of Foreign Taste)
1: none
2: subtly felt
3: slightly felt
4: felt
5: strongly sense (Evaluation Standards of Overall Judgment)
A: salty (4 or more), but without bitter and foreign tastes (1 or less)
B: salty (4 or more), and with slight bitter and foreign tastes (2 or less)
C: weak salty taste (or less), but without bitter and foreign tastes (1 or less), or alternatively, slightly weak salty taste (3 or less), and with slight bitter and foreign tastes (3 or less)
D: bitter and foreign tastes were felt (3 or more)

TABLE 1

| | | test example | | | | | | | | | | | | | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 |
| raw material | low-salt soy sauce A | | | | | | | 93.3 | 928 | | 92.8 | 91.8 | | 93.2 | 92.6 | 93.4 | 92.9 |
| | low-salt soy sauce B | | | | | | | | | 93.9 | | | 93.4 | | | | |
| | low-salt soy sauce C | 92.3 | 94.3 | 94.3 | | | | | | | | | | | | | |
| | low-salt soy sauce D | | | | 93.8 | 94.3 | 94.3 | | | | | | | | | | |
| | potassium chloride | 5 | 4 | 4 | 5 | 4 | 4 | 4 | 4 | 3 | 4 | 4 | 3 | 4 | 4 | 4 | 4 |
| | lactic acid | 0.5 | 0.5 | 0.5 | 0.45 | 0.45 | 0.45 | 0.45 | 0.45 | 0.5 | 0.45 | 0.45 | 0.5 | 0.45 | 0.45 | 0.45 | 0.45 |
| | citric acid | 0.04 | 0.04 | 0.04 | 0.05 | 0.05 | 0.05 | 0.05 | 0.05 | 0.04 | 0.05 | 0.05 | 0.04 | 0.05 | 0.05 | 0.05 | 0.05 |
| | malic acid | 0.04 | 0.04 | 0.04 | 0.05 | 0.05 | 0.05 | 0.05 | 0.05 | 0.04 | 0.05 | 0.05 | 0.04 | 0.05 | 0.05 | 0.05 | 0.05 |
| | disodium succinate | 0.06 | 0.06 | 0.06 | 0.08 | 0.08 | 0.08 | 0.08 | 0.08 | 0.06 | 0.08 | 0.08 | 0.06 | 0.08 | 0.08 | 0.08 | 0.08 |
| | disodium inosinate | 0.05 | 0.05 | 0.05 | 0.04 | 0.04 | 0.04 | 0.04 | 0.04 | 0.05 | 0.04 | 0.04 | 0.05 | 0.04 | 0.04 | 0.04 | 0.04 |
| | sodium aspartate monohydrate | | | | | | | 1 | 1 | 1.3 | 1 | 1 | 1.3 | 1 | 1 | 1 | 1 |
| | sodium glutamate monohydrate | | | | | | | 0.5 | 0.5 | 0.6 | 0.5 | 0.5 | 0.6 | 0.5 | 0.5 | 0.5 | 0.5 |
| | 4-aminobutyric acid | | | 1 | 0.5 | 1 | | 0.5 | 1 | 0.5 | | | | | | | |
| | taurine | 2 | 1 | | | | 1 | | | | 1 | 2 | 1 | | | | |
| | polyphenol preparation A | | | | | | | | | | | | | 0.63 | 1.25 | | |

TABLE 1-continued

|  |  |  |  |  |  |  |  |  |  |  |  |  |  |  |  |  |
|---|---|---|---|---|---|---|---|---|---|---|---|---|---|---|---|---|
|  | polyphenol preparation B |  |  |  |  |  |  |  |  |  |  |  |  |  |  | 0.46 | 0.92 |
|  | peptide A |  |  |  |  |  |  |  |  |  |  |  |  |  |  |  |  |
|  | peptide B |  |  |  |  |  |  |  |  |  |  |  |  |  |  |  |  |
| analytical value | Sodium concentration (% by weight) | 3.20 | 3.27 | 3.27 | 3.40 | 3.42 | 3.42 | 3.34 | 3.32 | 3.37 | 3.32 | 3.29 | 3.35 | 3.50 | 3.32 | 3.34 | 3.33 |
|  | salt concentration (% by weight) | 8.14 | 8.32 | 8.32 | 8.65 | 8.69 | 8.69 | 8.50 | 8.45 | 8.57 | 8.45 | 8.37 | 8.53 | 8.49 | 8.43 | 8.50 | 8.46 |
|  | potassium concentration (% by weight) | 2.86 | 2.34 | 2.34 | 2.98 | 2.46 | 2.46 | 2.52 | 2.52 | 1.89 | 2.52 | 2.51 | 1.88 | 2.52 | 2.52 | 2.52 | 2.52 |
|  | nitrogen concentration (% by weight) | 1.32 | 1.35 | 1.35 | 1.42 | 1.43 | 1.43 | 1.80 | 1.80 | 1.89 | 1.80 | 1.78 | 1.89 | 1.80 | 1.79 | 1.80 | 1.80 |
| evaluation | salty taste | 4 | 4 | 4 | 4 | 4 | 4 | 4 | 4 | 4 | 4 | 4 | 4 | 4 | 4 | 4 | 4 |
|  | bitter taste | 2 | 2 | 2 | 2 | 2 | 2 | 1 | 1 | 1 | 1 | 1 | 1 | 1 | 1 | 1 | 1 |
|  | foreign taste | 1 | 1 | 1 | 1 | 1 | 1 | 1 | 1 | 1 | 1 | 1 | 1 | 1 | 1 | 1 | 1 |
|  | overall judgment | B | B | B | B | B | B | A | A | A | A | A | A | A | A | A | A |

| | | test example ||||||||||||||| 
|---|---|---|---|---|---|---|---|---|---|---|---|---|---|---|---|
| | | 17 | 18 | 19 | 20 | 21 | 22 | 23 | 24 | 25 | 26 | 27 | 28 | 29 | 30 | 31 |
| raw material | low-salt soy sauce A | 88.8 | 88.8 |  |  |  |  |  |  |  |  |  | 93.8 |  |  |  |
|  | low-salt soy sauce B |  |  | 93.8 | 93.2 | 91.9 |  |  |  |  |  |  |  | 94.4 |  |  |
|  | low-salt soy sauce C |  |  |  |  |  | 100 |  | 99.5 | 99.4 | 98.8 | 95.0 |  |  | 98 |  |
|  | low-salt soy sauce D |  |  |  |  |  |  | 100 |  |  |  |  |  |  |  | 95 |
|  | potassium chloride | 4 | 4 | 3 | 3 | 3 |  |  |  |  |  |  | 4 | 3 | 2 | 5 |
|  | lactic acid | 0.45 | 0.45 | 0.5 | 0.5 | 0.5 |  |  |  |  |  |  | 0.45 | 0.5 |  |  |
|  | citric acid | 0.05 | 0.05 | 0.04 | 0.04 | 0.04 |  |  |  |  |  |  | 0.05 | 0.04 |  |  |
|  | malic acid | 0.05 | 0.05 | 0.04 | 0.04 | 0.04 |  |  |  |  |  |  | 0.05 | 0.04 |  |  |
|  | disodium succinate | 0.08 | 0.08 | 0.06 | 0.06 | 0.06 |  |  |  |  |  |  | 0.08 | 0.06 |  |  |
|  | disodium inosinate | 0.04 | 0.04 | 0.05 | 0.05 | 0.05 |  |  |  |  |  |  | 0.04 | 0.05 |  |  |
|  | sodium aspartate monohydrate | 1 | 1 | 1.3 | 1.3 | 1.3 |  |  |  |  |  |  | 1 | 1.3 |  |  |
|  | sodium glutamate monohydrate | 0.5 | 0.5 | 0.6 | 0.6 | 0.6 |  |  |  |  |  |  | 0.5 | 0.6 |  |  |
|  | 4-aminobutyric acid |  |  |  |  |  |  |  | 0.5 |  |  |  |  |  |  |  |
|  | taurine |  |  |  |  |  |  |  |  |  |  |  |  |  |  |  |
|  | polyphenol preparation A |  |  | 0.63 | 1.25 |  |  |  |  | 0.63 | 1.25 |  |  |  |  |  |
|  | polyphenol preparation B |  |  |  |  |  |  |  |  |  |  |  |  |  |  |  |
|  | peptide A | 5 |  |  |  | 2.5 |  |  |  |  |  | 5 |  |  |  |  |
|  | peptide B |  | 5 |  |  |  |  |  |  |  |  |  |  |  |  |  |
| analytical value | Sodium concentration (% by weight) | 3.19 | 3.19 | 3.37 | 3.50 | 3.31 | 3.19 | 3.20 | 3.17 | 3.17 | 3.15 | 3.03 | 3.36 | 3.39 | 3.13 | 3.04 |
|  | salt concentration (% by weight) | 8.11 | 8.11 | 8.56 | 8.49 | 8.41 | 8.11 | 8.13 | 8.07 | 8.06 | 8.01 | 7.70 | 8.54 | 8.62 | 7.95 | 7.72 |
|  | potassium concentration (% by weight) | 2.50 | 2.50 | 1.88 | 1.88 | 1.88 | 0.26 | 0.38 | 0.25 | 0.25 | 0.25 | 0.24 | 2.52 | 1.89 | 1.30 | 2.98 |
|  | nitrogen concentration (% by weight) | 1.72 | 1.72 | 1.89 | 1.88 | 1.86 | 1.42 | 1.51 | 1.41 | 1.41 | 1.40 | 1.35 | 1.81 | 1.90 | 1.39 | 1.43 |
| evaluation | salty taste | 4 | 4 | 4 | 4 | 4 | 1 | 1 | 1 | 1 | 1 | 1 | 4 | 4 | 2 | 3 |
|  | bitter taste | 2 | 2 | 1 | 1 | 1 | 1 | 1 | 1 | 1 | 1 | 4 | 1 | 1 | 2 | 3 |
|  | foreign taste | 2 | 2 | 1 | 1 | 2 | 1 | 1 | 1 | 1 | 1 | 4 | 1 | 1 | 1 | 1 |
|  | overall judgment | B | B | A | A | B | C | C | C | C | C | D | A | A | C | C |

(7) Measurement Method of Antihypertensive Effect (a) Tested Animals

Sixteen weeks old maleness spontaneous hypertensive rats (SHR) bred under the conditions in which room temperature was 25±1° C., humidity was 55±10% RH, and lighting hours were 12 hours (from 7 a.m. to 7 p.m.) (a breeding room within a rat area).

(b) Medication Method and Dosage

A physiological salt solution was used in a control area. Oral administration was taken as a way of medication, and the administration was compulsorily carried out by using a metal stomach tube. The dosage was 5 mL/kg.

(c) Testing Method

Three SHRs per group were used after they had been fasted. Systolic blood pressures of a caudal artery were measured before and 6 hours after the oral administration by using a commercially available noninvasive sphygmomanometer for rats (produced by Softron Corp.).

(d) Statistical Processing Method

The obtained measurement result was expressed as an average value of rate-of-change and the standard deviation (SE) thereof, and subjected to Student's T-test.

Test Examples 7, 13, 14, 17, 22, 24, 25, 26, 27, and 28 in Table 1 and an example which uses a physiological salt solution were investigated for their antihypertensive effect. The results are shown in FIG. 1.

From FIG. 1, it may be recognized that the liquid seasoning of the present invention provides an antihypertensive effect. In addition, it has been recognized that, from Table 1, even if a substance which has a lower sodium chloride concentration and also has an antihypertensive effect, the salty taste may be sufficiently sensed by adjusting the potassium concentration within a certain range described in the present invention, so that this is an adequate level for continuous consumption as soy sauce without the effort.

What is claimed is:

1. A liquid seasoning, comprising:
   (A) 3.55% by weight or less of sodium ion;
   (B) 0.5 to 3.6% by weight of potassium ion; and
   (C) 0.05 to 20% by weight of at least one polyphenol selected from the group consisting of catechin, epicatechin, gallocatechin, epigallocatechin, rutin, quercitrin, isoquercitrin, quercetin, myricitrin, myricetin, daizein, daizin, glycitein, glycitin, genistein, genistin, hesperidin, methylhesperidin, neohesperidin, hesperetin, naringin, naringenin, prunin, astragalin, kaempferol, apiin, apigenin, delphinidin, delphin, nasunin, peonidin, peonin, petunin, peonidin, malvidin, malvin, enin, cyanidin, leucocyanidin, cyanin, chrysanthemin, keracyanin, idein, mecocyanin, pelargonidin, and callistephin, or an acetylated product of said polyphenol, a malonylated product of said polyphenol, a methylated product of said polyphenol, or a sugar-binding product in which one or more sugar molecules selected from the group consisting of glucose, rhamnose, galactose, rutinose, neohesperidose, and apiosyl glucose are bound to one molecule of said polyphenol via a covalent bond,
   wherein the pH of the liquid seasoning is from 3 to 6.5.

2. The liquid seasoning according to claim 1, wherein said liquid seasoning is low-salt soy sauce.

3. The liquid seasoning according to claim 1, wherein said sodium ion is at a concentration of 1.18 to 3.55% by weight.

4. The liquid seasoning according to claim 1, wherein said sodium ion is at a concentration of 2.75 to 3.5% by weight.

5. The liquid seasoning according to claim 1, wherein said sodium ion is at a concentration of 3.1 to 3.4% by weight.

6. The liquid seasoning according to claim 1, wherein said sodium ion is at a concentration of 3.2 to 3.4% by weight.

7. The liquid seasoning according to claim 1, wherein said potassium ion is at a concentration of 1 to 3.6% by weight.

8. The liquid seasoning according to claim 1, wherein said potassium ion is in the form of potassium chloride.

9. The liquid seasoning according to claim 1, wherein said polyphenol is at a concentration of 0.1 to 10% by weight.

10. The liquid seasoning according to claim 1, wherein said polyphenol is at a concentration of 0.2 to 5% by weight.

11. The liquid seasoning according to claim 1, wherein the nitrogen content of said liquid seasoning is 1.6% by weight or more excluding the component (C) nitrogen content therefrom.

12. The liquid seasoning according to claim 11, further comprising:
   one or more of amino acids, sodium salts thereof, potassium salts thereof, or hydrochloride salts thereof selected from the group consisting of glycine, alanine, phenyl alanine, cystine, threonine, tyrosine, isoleucine, glutamic acid, aspartic acid, histidine, lysine, and arginine.

13. The liquid seasoning according to claim 1, further comprising:
   one or more nucleic acid seasoning, organic acid salt seasoning, or acidulant, wherein
   said nucleic acid seasoning is selected from the group consisting of a sodium salt of 5'-guanylic acid, a sodium salt of 5'-inosinic acid, a potassium salt of 5'-guanylic acid, a potassium salt of 5'-inosinic acid, a calcium salt of 5'-guanylic acid, and a calcium salt of 5'-inosinic acid;
   said organic acid salt seasoning is selected from the group consisting of a sodium salt of lactic acid, a sodium salt of succinic acid, a sodium salt of malic acid, a sodium salt of citric acid, a sodium salt of tartaric acid, a sodium salt of gluconic acid, a potassium salt of lactic acid, a potassium salt of succinic acid, a potassium salt of malic acid, a potassium salt of citric acid, a potassium salt of tartaric acid, and a potassium salt of gluconic acid; and
   said acidulant is selected from the group consisting of lactic acid, succinic acid, malic acid, citric acid, and tartaric acid.

14. The liquid seasoning according to claim 1, wherein the pH of the liquid seasoning is from 4 to 6.

15. The liquid seasoning according to claim 1, further comprising:
   one or more additives selected from the group consisting of ammonium chloride, calcium lactate, ethanol, mirin, brewed vinegar, and a sweetener.

16. The liquid seasoning according to claim 1, wherein the chlorine content thereof is 4 to 9% by weight.

17. The liquid seasoning according to claim 1, further comprising one or more compounds selected from the group consisting of caffeoylquinic acids, feruloylquinic acids, flavonols, flavanols, flavanones, flavones, isoflavones, and anthocyanidins.

18. The liquid seasoning according to claim 1, wherein the polyphenol is an acetylated product, a malonylated product, a methylated product, or a sugar-binding product of said compound.

19. The liquid seasoning according to claim 18, wherein the polyphenol is a sugar-binding product of said compound and wherein one or more molecules of sugars selected from the group consisting of glucose, rhamnose, galactose, rutinose, neohesperidose, and apiosyl glucose, are bound to one molecule of polyphenol via a covalent bond.

20. The liquid seasoning according to claim 19, wherein 1 to 20 molecules of sugar are bound to the polyphenol.

21. The liquid seasoning according to claim 19, wherein 2 to 10 molecules of sugar are bound to the polyphenol.

22. The liquid seasoning according to claim 1, further comprising caffeoylquinic acid is at least one caffeoylquinic acid selected from the group consisting of 3-caffeoylquinic acid, 4-caffeoylquinic acid, 5-caffeoylquinic acid (chlorogenic acid), 3,4-dicaffeoylquinic acid, 3,5-dicaffeoylquinic acid, 4,5-dicaffeoylquinic acid, 3-feruloylquinic acid, 4-feruloylquinic acid, 5-feruloylquinic acid, and 3-feruloyl-4-caffeoylquinic acid or salts thereof.

23. The liquid seasoning according to claim 1, wherein the polyphenol is hesperidin.

24. A method of seasoning food comprising blending the liquid seasoning according to claim 1 with said food.

25. A liquid seasoning, comprising:
   (A) 3.55% by weight or less of sodium ion;
   (B) 0.5 to 3.6% by weight of potassium ion; and
   (C) 0.05 to 20% by weight of at least one polyphenol selected from the group consisting of catechin, epicatechin, gallocatechin, epigallocatechin, rutin, quercitrin, isoquercitrin, quercetin, myricitrin, myricetin, daizein, daizin, glycitein, glycitin, genistein, genistin, hesperidin, methylhesperidin, neohesperidin, hesperetin, naringin, naringenin, prunin, astragalin, kaempferol, apiin, apigenin, delphinidin, delphin, nasunin, peonidin, peonin, petunin, peonidin, malvidin, malvin, enin, cyanidin, leucocyanidin, cyanin, chrysanthemin, keracyanin, idein, mecocyanin, pelargonidin, and callistephin, or a sugar-binding product in which one or more sugar molecules selected from the group consisting of glucose, rhamnose, galactose, rutinose, neohesperidose, and apiosyl glucose are bound to one molecule of said polyphenol via a covalent bond, wherein the pH of the liquid seasoning is from 3 to 6.5.

26. A liquid seasoning, comprising:
(A) 3.55% by weight or less of sodium ion;
(B) 0.5 to 3.6% by weight of potassium ion; and
(C) 0.05 to 20% by weight of at least one polyphenol selected from the group consisting of catechin, epicatechin, gallocatechin, epigallocatechin, rutin, quercitrin, isoquercitrin, quercetin, myricitrin, myricetin, daizein, daizin, glycitein, glycitin, genistein, genistin, hesperidin, methylhesperidin, neohesperidin, hesperetin, naringin, naringenin, prunin, astragalin, kaempferol, apiin, apigenin, delphinidin, delphin, nasunin, peonidin, peonin, petunin, peonidin, malvidin, malvin, enin, cyanidin, leucocyanidin, cyanin, chrysanthemin, keracyanin, idein, mecocyanin, pelargonidin, and callistephin, or a sugar-binding product in which one or more sugar molecules selected from the group consisting of glucose, rhamnose, galactose, rutinose, neohesperidose, and apiosyl glucose are bound to one molecule of said polyphenol via a covalent bond, wherein the chlorine content is 4 to 9% by weight.

* * * * *